United States Patent
Leti et al.

(10) Patent No.: US 12,186,354 B2
(45) Date of Patent: Jan. 7, 2025

(54) LESPEDEZA CAPITATA EXTRACT FOR USE IN THE FIELD OF HAIR CARE

(71) Applicant: PIERRE FABRE DERMO-COSMETIQUE, Boulogne-Billancourt (FR)

(72) Inventors: Mathieu Leti, Montgiscard (FR); Sylvie Daunes-Marion, Toulouse (FR); Marguerite Leveque, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 925 days.

(21) Appl. No.: 17/263,506

(22) PCT Filed: Jul. 19, 2019

(86) PCT No.: PCT/EP2019/069569
§ 371 (c)(1),
(2) Date: Jan. 26, 2021

(87) PCT Pub. No.: WO2020/020791
PCT Pub. Date: Jan. 30, 2020

(65) Prior Publication Data
US 2021/0169960 A1   Jun. 10, 2021

(30) Foreign Application Priority Data
Jul. 27, 2018 (FR) ..................... 1856999

(51) Int. Cl.
*A61K 36/48* (2006.01)
*A61P 17/08* (2006.01)
*A61P 17/14* (2006.01)

(52) U.S. Cl.
CPC .............. *A61K 36/48* (2013.01); *A61P 17/08* (2018.01); *A61P 17/14* (2018.01)

(58) Field of Classification Search
None
See application file for complete search history.

(56) References Cited

U.S. PATENT DOCUMENTS 4,460,578 A * 7/1984 Cervelle ................ A61K 36/48
424/757
2013/0078202 A1   3/2013   Abdul-Malak et al.

FOREIGN PATENT DOCUMENTS

| CN | 103251533 A | 8/2013 |
|---|---|---|
| EP | 1 226 827 A1 | 7/2002 |
| KR | 10-2013-0091406 A | 8/2013 |
| WO | WO 97/28814 A | 8/1997 |
| WO | WO 2018/127612 A2 | 7/2018 |

OTHER PUBLICATIONS

Pastorino et al. (2017) Industrial Crops and Products 96: 158-164. (Year: 2017).*
Raskin et al. (2004) Current Pharmaceutical Design 10, 3419-3429. (Year: 2004).*
Revilla et al. (1998) J. Agric. Food Chem. 46, 4592-4597 (Year: 1998).*
Shin et al. (2022) Appl. Sci. 12, 2863 (Year: 2022).*
Inui et al., "Molecular basis of androgenetic alopecia: From androgen to paracrine mediators through dermal papilla," Journal of Dermatological Science, vol. 61, No. 1, 2011, pp. 1-6.
Kwack et al., "Dihydrotestosterone-Inducible Dickkopf 1 from Balding Dermal Papilla Cells Causes Apoptosis in Follicular Keratinocytes," Journal of Investigative Dermatology, vol. 128, No. 2, 2008 (published online Jul. 26, 2007), pp. 262-269.
Leirós et al., "Hair follicle stem cell differentiation is inhibited through cross-talk between Wnt/β-catenin and androgen signalling in dermal papilla cells from patients with androgenetic alopecia," British Journal of Dermatology, vol. 166, No. 5, 2012, pp. 1035-1042.
Pastorino et al., "Biological activities of the legume crops *Melilotus officinalis* and *Lespedeza capitata* for skin care and pharmaceutical applications," Industrial Crops and Products, vol. 96, 2017, pp. 158-164.
Yarnell et al., "Herbs for Relieving Chronic Renal Failure," Alternative and Complementary Therapies, vol. 13, No. 1, Feb. 2007, pp. 18-23.
Yarnell, "Botanical Medicines Used for Kindey Disease in the United States," IJKD, vol. 6, 2012, pp. 407-418.
Geyfman et al., "Clock genes, hair growth and aging", Aging, vol. 2, No. 3, Mar. 2010, pp. 122-128.

* cited by examiner

*Primary Examiner* — Russell G Fiebig
(74) *Attorney, Agent, or Firm* — Birch, Stewart, Kolasch & Birch, LLP

(57) ABSTRACT

The present invention relates to an extract of *Lespedeza capitata* Michx., for use in cosmetics and/or dermatology in the field of hair care and, more specifically, in the treatment and/or prevention of alopecia and/or seborrhea of the scalp.

6 Claims, No Drawings

LESPEDEZA CAPITATA EXTRACT FOR USE IN THE FIELD OF HAIR CARE

TECHNICAL FIELD

The present invention concerns a *Lespedeza capitata* Michx. extract for its use in cosmetics and/or dermatology in the hair care field; more particularly in the treatment and/or prevention of alopecia and/or scalp seborrhea.

PRIOR STATE OF THE ART

*Lespedeza capitata* Michx. is a herbaceous perennial of the Leguminosae family originating from North America. *Lespedeza capitata* Michx. is cultivated in Europe and particularly in France.

*Lespedeza capitata* Michx. is a tomentose plant whose erect stems can reach a height of 1.5 meters. Its leaves are alternate, compound and generally trifoliate; the leaflets measure approximately 4.5×1.8 cm; the petiole is short (2-5 mm). The leaves and stems are covered with appressed hairs that can give the plant a silver sheen. The flowers are papilionaceous and densely grouped into axillary inflorescences. The petals are white except for the standard, which has a pink to purple tinge. The calyx is persistent and takes on a brown tint over time. The fruits are indehiscent and bear a single seed. *Lespedeza capitata* Michx. is deeply rooted, with primary roots that can burrow up to 2.5 meters in the ground.

*Lespedeza capitata* Michx. is part of the traditional medicine of many Native American ethnicities. The Omaha and Ponca used the stems as a moxa to treat rheumatism or neuralgia. The Comanche used the leaves in the form of an infusion. The Meskwaki used the root as a antidote for poisoning (USDA-NRCS. Plant Guide 5 Dec. 2000). Currently, *Lespedeza capitata* Michx. is mainly cultivated for its use in dietary supplements and pharmaceutical, homeopathic and veterinary preparations The aerial parts of *Lespedeza capitata* Michx. have essentially been studied for their properties in the urinary sphere (particularly their diuretic and anti-azotemic capacity). Several clinical studies have been documented. The majority were conducted in the 60s to 80s, mainly in France. The clinical studies particularly relate to the administration of *Lespedeza capitata* Michx. extracts intravenously to patients with kidney disease. The cholesterol-lowering activity of a tincture of *Lespedeza capitata* Michx. administered orally has been documented in a clinical study conducted in 39 subjects with stable hypercholesterolemia (Yarnell and Abascal, Alternative and Complementary Therapies. 13(1): 18-23, 2007).

The aerial parts of *Lespedeza capitata* Michx. are still used today for their therapeutic properties. Powdered or in the form of extracts, they are marketed for the preparation of infusions, as dietary supplements, homeopathic or pharmaceutical preparations (azotemia; urinary sphere) or veterinary preparations (urinary sphere).

One recent publication shows that the ethanol extract of *Lespedeza capitata* Michx. induces in vitro the proliferation of fibroblasts and keratinocytes, inhibition of collagenase and stimulation of collagen synthesis by fibroblasts and has a lipolytic action (Pastorino et al. 2017. Industrial Crops and Products. 96: 158-164). Patent application CN104606122 has also claimed that *Lespedeza capitata*, in mixture with other plants, is able to burn pregnancy-related abdominal fat.

SUMMARY OF THE INVENTION

Unexpectedly and surprisingly, the applicants showed that a *Lespedeza capitata* Michx. extract has pharmacological activities of interest in the field of treatment and/or prevention of skin and hair disorders and especially for combatting hair loss and for treating scalp seborrhea and associated disorders.

Indeed, the inventors showed that a *Lespedeza capitata* Michx. extract inhibits the synthesis and release of Dickkopf-related protein 1 (DKK1) by the cells of the dermal papilla. Thus, *Lespedeza capitata* Michx. will help to delay and prevent hair loss and extend the life cycle of the hair.

Furthermore, the inventors have shown that an *Lespedeza capitata* Michx. extract inhibits 5α-reductase activity in dermal papilla cells. Consequently, *Lespedeza capitata* Michx. extract will be useful in the field of hair loss prevention as well as in scalp seborrhea and associated skin and hair disorders.

This new use of *Lespedeza capitata* Michx. in the hair care field is the subject of the present invention and makes it possible to envision the application of various *Lespedeza capitata* Michx.-based products to improve the esthetic appearance of the hair by care thereof, as well as to prevent and/or treat hair loss and/or scalp seborrhea and all associated skin and hair disorders.

The invention therefore also concerns a *Lespedeza capitata* extract for its use for the treatment and/or prevention of at least one skin and hair disorder.

Advantageously, said skin and hair disorder is chosen from among alopecia, scalp seborrheic dermatitis, scalp erythema, scalp seborrhea and combinations thereof. The skin and hair disorder may also be oily hair.

DETAILED DESCRIPTION

Hair care for not just cosmetic purposes, but also to prevent hair loss and regenerate hair, is always interesting to researchers.

The hair follicle is a mini-organ anchored in the skin up to the hypodermis whose main function is to produce a hair shaft. The hair follicle is a dynamic structure that produces hair. Hair does not grow continuously but rather according to a hair growth cycle divided into three phases:

- A growth phase (anagen): The dermal papilla cells (fibroblasts) send a signal to the stem cells of the bulb which allows their proliferation. These cells will be transformed and envelop the dermal papilla to form the sulphur matrix of the hair. They divide and differentiate into keratinocytes, cells responsible for hair structure. For the hair to be properly structured, keratinocytes need sulphur-containing proteins, vitamin B6 and various minerals such as zinc and magnesium. The duration of this phase determines the length of the hair and depends on the proliferation and differentiation of the matrix cells at the base of the follicle.
- A regression phase (catagen): The matrix dies and, as a result, the dermal papilla is no longer in contact with this matrix. There is no longer an exchange between the cells. The follicle and dermal papilla move up to the epidermis.
- A rest phase (telogen): The dermal papilla and bulb cells are intact and inactive. The hair falls out. For new hair to grow, the cycle must be reinitiated.

The hair renews itself continuously and out of the 100,000 to 150,000 strands making up the hair, the majority are in the growth phase. Normal physiological hair loss is around 60 to 100 strands a day for healthy hair. Beyond this, the loss is considered pathological, whether occasional or ongoing.

The term alopecia designates partial or general hair loss. Many factors may be involved in alopecia, such as, for example, genetic factors, age, sex, disease, stress, hormonal problems, drug side effects and injuries. Several forms of alopecia can be distinguished:

Hereditary androgenetic alopecia is the most common. Early hair loss occurs in genetically-predisposed subjects and particularly affects men. It is manifested by a decrease in hair volume or even baldness and affects 50% of men over 50 years old;

Postmenopausal alopecia is the most common cause of boldness in women. In women, hair loss is more diffuse and spread out than in men. Diffuse female alopecia is a disorder that often starts at menopause and concerns approximately 40% of elderly women above age 70. The term diffuse illustrates that, unlike in men, hair loss involves all of the hair on the head evenly;

Acute or reactive alopecia may be linked to chemotherapy treatment, stress, childbirth, major dietary deficiencies, iron deficiency and hormonal disorders. It is a simultaneous and diffuse loss of a substantial quantity of hair;

Scarring alopecia can be caused by skin problems (tumor, burn, alopecia areata), acute irradiation, lupus erythematosus or parasites (ringworm, lichen);

Alopecia areata appears to be of autoimmune origin and is characterized by damage in variably-sized patches in one or more places;

Congenital alopecia is rare and is an absence of hair roots or hair anomalies (mutations).

Alopecia is essentially linked to a disruption of hair renewal that leads first to acceleration of cycle frequency at the expense of the quality of hair and then the quantity thereof. The most common phenomenon is a reduction in the growth cycle (anagen phase) due to a shutdown of cellular proliferation. The consequence is a premature induction of the catagen phase and a greater number of hair follicles in the telogen phase and therefore greater hair loss. To combat alopecia, it is therefore necessary to relaunch the hair cycle, for example by activating the anagen phase.

It is currently known that the mechanisms responsible for hereditary androgenetic alopecia (also called seborrheic alopecia) involve, among other things, hormonal components with the overexpression of the androgen receptor (testosterone and DHT receptor) and a more intense activity of the 5-alpha-reductase enzyme. This hormonal dysregulation leads to an excessive production of dihydrotestosterone (DHT), the active metabolite of testosterone. At the dermal papilla, this metabolite will stimulate the production of hair cycle inhibitors leading to shortening of the anagen phase, forcing the hair to go too quickly into the telogen phase and not allowing the hair follicle enough time to produce quality keratin and, necessarily, after several cycles, an exhaustion of the capacity of the hair follicle to produce a hair shaft.

This alopecia due to an excess of androgens also affects women during menopause (postmenopausal alopecia) or following treatment with androgens. It starts at the temples and crown. This hair loss is more diffuse and spread out than in men. The hair loss concerns the entire scalp evenly.

A 5-alpha-reductase inhibitor therefore allows treating and/or preventing hair loss in men and/or women.

Seborrhea is an excessive production of sebum by the sebaceus glands. Overall, humans have 2,000,000 sebaceus glands annexed to 6,000,000 hairs. The distribution of sebaceus glands is not uniform. The density of sebaceus glands reaches 300 to 900 sebaceus glands/$cm^2$ on the face and scalp, and this density is around 100 sebaceus glands/$cm^2$ in the upper part of the chest and back. Sebaceus gland activity is influenced by androgens. Androgens are only active under the influence of the 5-alpha-reductase enzyme that ensures the metabolization of androgens in the sebaceus gland that induces the production of sebum. Hyperactivation of the 5-alpha-reductase enzyme induces seborrhea.

The site of the manifestations of seborrhea is the medial facial region (forehead, nose, chin) where the sebaceus glands are the most numerous and largest. Seborrhea is also manifested at the scalp where it predominates in the frontal and frontotemporal regions and at the top of the cranium.

Scalp seborrhea causes esthetic and dermatological conditions such as scalp seborrheic dermatitis and scalp erythema.

Scalp seborrheic dermatitis (SD) is characterized by diffuse, pink, inflammatory patches, covered in oily, white, crusty scales, adhering to the epidermis, sometimes purulent and sometimes causing severe itching.

Seborrhea is often associated with androgenetic alopecia.

An active inhibitor of the 5α-reductase enzyme would therefore make it possible to reduce sebum secretion, treat seborrhea and resolve the dermatological and/or esthetic problems related to seborrhea.

The hair growth cycle is a highly-regulated process during which the various compartments of the hair follicle (dermal papilla, stem cells residing in the bulb, keratinocytes of the hair follicle matrix) enter into close relationships through various molecular exchanges. Among the signals involved, the Wnt/β-catenin signal is known to promote hair growth (Leiros et al., Br. J. Dermatol. 166(5)-1035-1042, 2012).

Androgenetic alopecia, which is the most common form of hair loss, is clearly an androgenic disease. Androgens dysregulate the factors secreted by the dermal papilla, which leads to a failure of stem cell differentiation by inhibition of the canonical Wnt signalling pathway.

The hair growth cycle inhibitor "Dickkopf-related protein 1 (DKK1)" is known to block the canonical activation of the Wnt pathway mediated by β-catenin and promote the progression of the catagen phase (Kwack et al., J. Invest. Dermatol. 132(6):1554-60, 2012). DKK1 is also described as being regulated by androgens (Kwack et al., J. Invest. Dermatol. 128(2):262-9, 2008).

Taken together, these results show that DKK1 plays an important role in the suppression of hair growth induced by androgens and the early induction of the catagen phase in androgenetic alopecia (Inui and Itami, J. Dermatol. Sci. 61(1):1-6, 2011).

Extract According to the Invention

In the present description, the *Lespedeza capitata* Michx. plant can be designated *Lespedeza capitata* for short.

In the context of the present invention, the *Lespedeza capitata* extract is obtained from one or more parts of the *Lespedeza capitata* plant chosen from among the roots and aerial parts such as stems, branches, leaves, fruits, seeds and/or flowers. Advantageously, it is the aerial parts chosen from among leaves, stems or flowers alone or in mixture.

In a particular embodiment of the invention, the extract is obtained from leaves and/or stems and/or flowers of *Lespedeza capitata*, especially dried.

In a particular embodiment of the invention, the extract is obtained from a culture of *Lespedeza capitata* cells.

According to a particular embodiment, the extract is a hydroalcoholic extract, in particular a hydroethanolic extract. Advantageously, it will be an extract resulting from a hydroalcoholic extraction, in particular hydroethanolic.

According to a preferred embodiment, the extract according to the invention can be obtained by a process according to the invention described below.

The *Lespedeza capitata* plant or part thereof can be fresh or dried, whole, cut or crushed and then subjected to an extraction step.

A preparation process of an extract according to the invention will comprise an extraction step of all or part of the *Lespedeza capitata* plant by a hydrophilic to nonpolar solvent, preferably a hydrophilic to moderately polar aqueous solvent.

"Moderately polar solvent" designates, within the meaning of the present invention, a solvent chosen from the group consisting of C1 to C5 alcohols, glycols (propylene glycol, butylene glycol, pentylene glycol), glycerol, acetone, alkyl esters (such as ethyl acetate and isopropyl acetate, in particular), mixtures of water-miscible solvents such as a hydroalcoholic mixture or an acetone/water mixture for example, or even hydrotropic solvents. The group of alternative hydrotropic solvents are amphiphilic molecules soluble in water which, from a sufficient concentration, can be extracted in moderately polar compounds such as described in the characterization of the extract.

Within the meaning of the present invention, "alkyl esters" designates an $R_1$—COO—$R_2$ compound wherein $R_1$ and $R_2$ are identical or different ($C_1$-$C_6$)alkyl groups. The ester may particularly be an acetate, i.e., a $CH_3COO$—$R_2$ compound.

Within the meaning of the present invention, "($C_1$-$C_6$) alkyl" group means a linear or branched hydrocarbon chain comprising 1 to 6 carbon atoms, preferably 1 to 4 carbon atoms. Examples include methyl, ethyl, propyl, isopropyl, butyl, isobutyl, sec-butyl, tert-butyl, pentyl or hexyl groups.

Within the meaning of the present invention, "nonpolar solvent" designates a solvent chosen from among heptane, hexane, limonene, halogenated hydrocarbons (chloroform, dichloromethane), supercritical $CO_2$ and a mixture of supercritical $CO_2$+ethanol.

It is understood that the choice of a nonpolar solvent such as defined above for the extraction is not preferred.

"Hydrophilic solvent" means a solvent chosen in the group made up of water, subcritical water, alcohols miscible with water (for example ethanol), C3 to C5 glycols, glycerol, acetone, and mixtures thereof.

"Aqueous solvent" designates a solvent chosen in the group made up of water alone and water in combination with subcritical water, alcohols miscible with water (for example ethanol), C3 to C5 glycols, glycerol, acetone, and mixtures thereof.

Within the meaning of the present invention, "dry extract" designates an extract with no extraction or carrier solvent, or only containing solvent in the state of an insignificant trace. Such a dry extract therefore contains only the material derived from *Lespedeza capitata*. It may also contain insignificant traces of extraction solvent.

In a preferred embodiment of the invention, the extraction solvent can be chosen from among ethyl acetate, isopropyl acetate, a C1 to C5 alcohol, a C3 to C5 glycol, glycerol or water or a mixture thereof. Preferentially it will be water or a water/alcohol mixture. Advantageously it will be an ethanol/water mixture.

Even more advantageously, this ethanol/water mixture will be characterized by a ethanol/water proportion of 9:1 to 7:3 (v/v).

Still more advantageously, the moderately polar solvent is an ethanol/water mixture in the proportion 9:1 (v/v).

According to another particular embodiment of the invention, the extraction is done with stirring or statically, at reflux, at ambient temperature or at a temperature comprised between ambient temperature and reflux. It may be assisted by ultrasound, microwave or extrusion in a plant weight/solvent volume ratio from 1/3 to 1/30, for a duration from 1 minute to 48 hours. The extraction can be repeated 2 to 3 times.

According to another particular embodiment of the invention, the solid phase is then separated by centrifugation or filtration in order to recover a clear liquid phase free of particles. Filtration can be done through a paper filter or filtration plate with a cutoff threshold comprised between 5 and 20 µm, particularly between 10 and 20 µm. Suitable filters or filtration plates can be chosen from the Pall® series K line of depth filtration products. Such plates are composed of a balanced mixture of cellulose fibers, diatomaceous earth and perlite, which allows a well-defined matrix to be created. Therefore, Pall® K300 to K900 series k plates can be chosen, for example. The liquid phase representing the extract can be concentrated to a greater or lesser extent, up to the point of obtaining a dry extract.

In another embodiment of the invention, a carrier can be added during the concentration step to obtain an extract containing 1 to 75% of dry extract. The carrier can be maltodextrin, lactose, silica, glycerin, a glycol, or any other cosmetologically-acceptable carrier that solubilizes the extract, preferably of biobased origin such as, for example, biobased glycols (1,2-pentanediol; 1,3-butanediol; 1,3-propanediol, etc.), and also hydrotropes such as, for example, alkyl glycosides (Sepiclear, Apyclean, APXC4, etc.).

According to a particular embodiment of the invention, color can be removed from the extract, for example by activated carbon, so as to eliminate all or part of the chlorophylls.

According to a particular embodiment of the invention, the *Lespedeza capitata* extract according to the invention is characterized by a content of 2 to 40%, particularly 5 to 35%, more particularly 10 to 30%, still more particularly approximately 25%, of total polyphenols (% by weight relative to the weight of the dry extract) expressed in grams of epicatechin per 100 grams of dry extract.

In the present invention, "approximately" means that the value concerned can be 10% lower or higher, especially 5%, in particular 1%, than the value indicated.

Composition According to the Invention

Another subject of the invention relates to a cosmetic, dermatological or skin and hair composition, comprising at least one extract of *Lespedeza capitata* according to the invention with at least one cosmetically or dermatologically-acceptable excipient, intended for the care of the hair and/or the scalp.

In the present invention, "cosmetically or dermatologically-acceptable" means something useful in the preparation of a cosmetic, dermatological, or skin and hair compound, which is generally safe, nontoxic and not biologically or otherwise undesirable and which is acceptable for cosmetic, dermatological or skin and hair use, particularly by topical application to the hair and/or scalp.

"Topical application" means application on the skin, especially the scalp, the mucosa and/or the integuments, especial on the hair and scalp.

"Integument" means head and body hair, eyebrows, eyelashes and/or nails, preferably hair of the head.

In a particular embodiment of the invention, the composition according to the invention is characterized in that it is present in an appropriate form for topical administration to the scalp and/or hair.

In a particular embodiment of the invention, the compositions according to the invention are intended for topical application, especially by application of the composition onto the scalp and/or hair and integuments.

The composition according to the invention can thus be presented in the commonly-known forms for topical administration, i.e., notably lotions, balms, shampoos, mousses, gels, dispersions, emulsions, sprays, serums, masks or creams, with excipients that allow penetration in order to improve the properties and accessibility of the active ingredients.

Advantageously, compositions according to the invention can be present in the commonly-known forms for topical administration onto the hair and scalp, i.e., especially a shampoo, a conditioner, a hair cream, a hair lotion, a mask or a no-rinse spray. They are therefore cosmetic, dermatological or skin and hair compositions.

Thus products that are formulated to be rinsed and products that do not require rinsing are distinguished.

In a particular embodiment of the invention, the composition according to the invention is characterized in that it is present in an appropriate form for oral administration. It has actually been shown that *Lespedeza capitata* can inhibit the renin-angiotensin system conversion enzyme, even when it is administered orally (Yarnell, 2012, IJKD, vol 6, 407-418). This extract is therefore not completely metabolized by its gastrointestinal passage.

According to another embodiment of the invention, compositions according to the invention can also be present in commonly-known forms for oral administration, i.e., notably tablets, capsules, powders, granules and oral solutions or suspensions. When a solid composition is prepared in the form of tablets, the main active ingredient is mixed with a pharmaceutical carrier such as gelatin, starch, lactose, magnesium stearate, talc, gum arabic, or the like. The tablets can be coated with sucrose or other appropriate materials or even be treated so that they have an extended or delayed activity and so that they continuously release a predetermined quantity of active ingredient.

A capsule preparation is obtained by mixing the active ingredient with a diluent and pouring the mixture obtained into hard or soft capsules.

In addition to the extract according to the invention, these compounds contain a physiologically-acceptable medium, in general water or solvent based, for example alcohols, ethers or glycols. They can also contain surfactants, complexing agents, preservatives, stabilizers, emulsifiers, thickeners, gelling agents, humectants, emollients, trace elements, essential oils, fragrances, dyes, moisturizers or thermal waters, etc.

In one embodiment, the cosmetic or dermatological compositions, in particular skin and hair compositions, according to the present invention will comprise from 0.0001% to 2%, preferably 0.001 to 1% by weight, preferably 0.005% to 0.8% by weight, more preferably 0.01% to 0.5% of *Lespedeza capitata* extract, by weight of dry extract relative to the total weight of the composition.

The *Lespedeza capitata* extracts used in the compositions according to the invention will advantageously comprise a dry extract content from 1% to 10%, preferably 1% to 5%, by weight relative to the total weight of the extract.

In a particular embodiment, the *Lespedeza capitata* extract is the only active agent used in the composition intended for hair and/or scalp care. Active agent means a curative or preventative agent for the skin and hair disorders targeted by the invention.

The extract according to the invention or the cosmetic or dermatological composition according to the invention can also be used in combination with a treatment for alopecia, such as finasteride or minoxidil, and/or in combination with compounds useful for a good hair structure, such as, for example, sulphur-containing proteins, vitamin B6 and various minerals such as zinc and/or magnesium.

The extract or composition according to the invention can also be combined with at least one antibacterial agent, an antifungal agent, an antiinflammatory and mixtures thereof.

The extract according to the invention or the cosmetic or dermatological composition according to the invention can be used in an individual who has had a micro-graft.

Preferably, the composition according to the invention has a light texture also permitting optimal penetration without making the hair or scalp greasy. From the first applications, the hair will regain strength and vitality.

The invention therefore also concerns a dermatological composition according to the invention for its use for the treatment and/or prevention of at least one skin and hair disorder.

The composition according to the invention for its use for the treatment and/or prevention of at least one skin and hair disorder is characterized in that the at least one skin and hair disorder is chosen from among alopecia, scalp seborrheic dermitis, scalp erythema, scalp seborrhea and combinations thereof.

The composition according to the invention for the treatment and/or prevention of at least one skin and hair disorder is characterized in that alopecia is chosen in the group consisting of androgenetic alopecia, reactive alopecia, postmenopausal alopecia and alopecia aerata.

Another object of the present invention concerns a dermatological composition comprising a *Lespedeza capitata* extract according to the invention for its use in the prevention and/or treatment of alopecia.

In a particular embodiment of the invention, the alopecia is chosen in the group consisting of androgenetic alopecia, postmenopausal alopecia, reactive alopecia and alopecia aerata.

According to another aspect, the invention relates to a cosmetic use of the extract according to the invention according to a method described above or of the cosmetic or dermatological composition according to the invention according to a method described above, for care of the hair and/or of the scalp, to limit hair loss, and/or promote hair growth and/or increase the density of hair follicles and/or obtain more covering hair and/or promote follicular regeneration, and/or reduce scalp seborrhea, and/or make the hair less oily.

In another aspect, the invention relates to a cosmetic treatment method for the hair and/or scalp in order to limit hair loss, and/or promote hair growth and/or increase the density of hair follicles and/or obtain more covering hair and/or promote follicular regeneration, and/or reduce scalp seborrhea, and/or make the hair less oily comprising the administration of an extract according to the invention to a person in need thereof. This administration may be topical or oral.

The invention therefore relates to a cosmetic use for a *Lespedeza capitata* extract according to the invention to limit hair loss, and/or promote hair growth and/or increase the density of hair follicles and/or obtain more covering hair and/or promote follicular regeneration, and/or reduce scalp seborrhea, and/or make the hair less oily.

Alternatively, the invention relates to the cosmetic use of a cosmetic composition according to the invention for care of the hair and/or of the scalp, to limit hair loss, and/or promote hair growth and/or increase the density of hair follicles and/or obtain more covering hair and/or promote follicular regeneration, and/or reduce scalp seborrhea, and/or make the hair less oily.

The invention also concerns a cosmetic method for care of the hair and/or of the scalp, to limit hair loss, and/or promote hair growth and/or increase the density of hair follicles and/or obtain more covering hair and/or promote follicular regeneration, and/or reduce scalp seborrhea, comprising the administration to an individual in need of an effective amount of an extract according to the invention according to a method described previously or of a cosmetic or dermatological composition according to the invention according to a method described previously.

In another aspect, the invention relates to a cosmetic treatment for the hair and/or scalp in order to limit hair loss, and/or promote hair growth and/or increase the density of hair follicles and/or obtain more covering hair and/or promote follicular regeneration, and/or reduce scalp seborrhea, and/or make the hair less oily comprising the administration of a cosmetic composition according to the invention to a person in need thereof. This administration is preferentially done topically to the hair and/or scalp.

The extract or the cosmetic or dermatological composition according to the invention will advantageously be administered topically and/or orally.

A composition according to the invention such as described here is characterized in that it is present in an appropriate form for topical administration to the scalp and/or hair.

A composition according to the invention such as described here is characterized in that it is present in an appropriate form for oral administration.

The extract according to the invention or the cosmetic or dermatological composition according to the invention also helps to stop hair loss by prolonging its cycle, so that the hair capital is preserved, in quantity and quality.

According to another aspect, the present invention also concerns a cosmetic hair care process intended to improve the esthetics of the hair by promoting hair growth and/or by promoting the production of more covering hair and/or by limiting hair loss, characterized in that it comprises the application to the hair and/or the scalp of an effective amount of a *Lespedeza* extract according to the invention or of a composition according to the invention, leaving the composition in contact with the hair and/or the scalp, and, optionally, rinsing the hair and the scalp.

According to another aspect, the present invention also concerns a cosmetic hair care process intended to improve the esthetics of the hair by combatting oily hair and/or restoring shine to dull hair and/or cleaning the oily scalp, characterized in that it comprises the application to the hair and/or the scalp of an effective amount of a *Lespedeza* extract according to the invention or of a composition according to the invention, leaving the composition in contact with the hair and/or the scalp, and, optionally, rinsing the hair and the scalp.

The examples that follow are intended to illustrate the invention without limiting the scope thereof. They are given by way of non-limiting example.

EXAMPLES

Preparation of an Extract Used for the Invention

Example 1: Reflux Extraction with Ethanol 90

2.5 kilograms of dried and crushed aerial parts of *Lespedeza capitata* are reflux extracted with stirring by 25 liters of a 90:10 (v/v) ethanol/water mixture for 1 hour in a reactor. The extract is then filtered through a K900 and the solvent is evaporated so as to obtain 250 grams of a green powder with a mass yield of 10%. The dry extract obtained contains 26% of polyphenols expressed in epicatechin.

Example 2: Reflux Extraction with Ethyl Acetate 100 grams of dried and crushed aerial parts of *Lespedeza capitata* are reflux extracted with stirring by 1 liter of ethyl acetate for 1 hour in a reactor. The extract is then filtered through a K900 and the solvent is evaporated so as to obtain 2 grams of a green paste with a mass yield of 2%. The dry extract obtained contains 3% of polyphenols expressed in epicatechin.

Example 3: Extraction at Ambient Temperature with Ethanol 30

20 kilograms of dried and crushed aerial parts of *Lespedeza capitata* are extracted at ambient temperature with stirring by 350 liters of a 30:70 (v/v) ethanol/water mixture for 12 hours in a reactor. The extract is then filtered through a K900 and the solvent is evaporated so as to obtain 3.4 grams of a brown powder with a mass yield of 17%. The dry extract obtained contains 36% of polyphenols expressed in epicatechin.

Example 4: Extraction with Ethanol 90 Assisted by Ultrasound Followed by Removing Color with Activated Carbon 26 grams of dried and crushed aerial parts of *Lespedeza capitata* are contacted with 260 milliliters of a 90:10 (v/v) ethanol/water mixture then extracted under the action of ultrasound (20 kHz) for 3 times 1 minute at an amplitude of 100%. After filtration through K900, the extract is concentrated and the color is removed with activated carbon (0.2% w/v). After filtration, the solvent is evaporated so as to obtain 1.5 grams of a brown powder with a mass yield of 6%. The dry extract obtained contains 25% of polyphenols expressed in epicatechin.

Example 5: Reflux Extraction with Ethanol 90 and Removing Color with Activated Carbon 280 grams of dried and crushed aerial parts of *Lespedeza capitata* are reflux extracted with stirring by 2800 milliliters of a 90:10 (v/v) ethanol/water mixture for 1 hour in a reactor. After filtration through K900, the extract is concentrated and the color is removed with activated carbon (0.2% w/v). After filtration, the solvent is evaporated so as to obtain 25 grams of an extract in the form of a brown powder with a mass yield of 9%. The extract obtained contains 25% of polyphenols expressed in epicatechin.

Example 6: Reflux Extraction with Ethanol 90 Followed by Removing Color with Activated Carbon and Putting in a Carrier 2.5 kilograms of dried and crushed aerial parts of *Lespedeza capitata* are reflux extracted with stirring by 25 liters of a 90:10 (v/v) ethanol/water mixture for 1 hour in a reactor. After filtration through K900, the extract is concentrated and the color is removed with activated carbon (0.2% w/v). After filtration, the extract is dried in 1,2-pentanediol so as to obtain 46 grams of extract in the form of a dark, viscous liquid. The extract obtained contains 50% of 1,2-pentanediol and 12% of polyphenols expressed in epicatechin.

Example 7: Reflux Extraction with Ethanol 90

100 grams of dried and crushed *Lespedeza capitata* leaves are reflux extracted with stirring by 1 liter of a 90:10 (v/v) ethanol/water mixture for 1 hour in a reactor. The extract is then filtered through a K900 and the solvent is evaporated so as to obtain 17 grams of a green powder with a mass yield of 17%. The dry extract obtained contains 28% of polyphenols expressed in epicatechin.

Pharmacological Assessment

Example 8: Inhibition of the Synthesis and Release of DKK1 by Dermal Papilla Cells by an Extract of Aerial Parts of *Lespedeza capitata*

This study aims to assess the effect of an extract according to the present invention on the production and secretion of DKK1 by dermal papilla cells of the human hair follicle and assess the dermatological and cosmetic value of this extract as a hair loss prevention agent. DKK1 has been shown to be a key factor in androgenic alopecia (see Kwack et al, BMB Reports, Volume 43, Issue 10, 2010, p. 688-692)

Experiments were conducted on dermal papilla cells of human hair follicles originating from three different donors.

The cells were inoculated on 96-well plates and cultured for 24 hours in standard culture media. The medium is then replaced by a test medium containing the compound to be tested or not (control condition). The *Lespedeza capitata* is an extract prepared according to Example 5 of the present invention and this extract is tested at two concentrations, 3 µg/ml and 10 µg/ml; it is a dry extract diluted in DMSO. Twenty-four hours later, the culture supernatants are collected and stored at −80° C.

The DKK1 protein was quantified by Luminex (kit reference: HBNMAG-51K, Millipore) according to the manufacturers instructions.

The raw data are analyzed by Microsoft Excel and Prism software. The statistical analysis is done by intergroup comparison with ANOVA followed by a Dunnett's test.

Results

Table 1 below shows DKK1 expression in the presence or absence of *Lespedeza capitata* and its percentage of inhibition

|  | Conc. | Mean [DKK1] µg/ml | sem | % inh | Stats |
|---|---|---|---|---|---|
| Control | — | 145.9 | 19.2 | — | — |
| Lespedeza | 3 µg/ml | 104.2 | 11.4 | 28 | $p < 0.01$ |
| extract | 10 µg/ml | 40.5 | 5.2 | 72 | $p < 0.01$ |

Con: concentration; sem: standard error of the mean; % inh % of inhibition relative to the control condition; Stats: statistic.

Human follicle dermal papilla cells naturally secrete DKK1 at around 150 pg/ml. When these cells are treated with a *Lespedeza capitata* extract, the expression of this protein is reduced in a concentration-dependent manner and significantly from the concentration of 3 µg/ml. In the presence of 10 µg/ml of *Lespedeza capitata* extract, the reduction of DKK1 reaches 72%.

The inventors thus demonstrated that a *Lespedeza* extract has an inhibitor activity on the DKK1 target.

Therefore, this extract has an interesting activity for its use as an agent in the prevention and/or treatment of hair loss.

Example 9: Inhibition of the Synthesis of 5α-Reductase by Dermal Papilla Cells by an Extract of Aerial Parts of *Lespedeza capitata*

This study aims to assess the effect of an extract according to the present invention on 5α-reductase activity in dermal papilla cells in order to measure the value of this extract in the field of hair loss prevention and or scalp seborrhea.

Experiments were conducted on dermal papilla cells of human hair follicles originating from two different donors. The cells were inoculated (150,000 cells per well) onto 24-well plates and cultured for 24 hours in standard culture media. The medium is then replaced by a test medium containing the compound to be tested or not (control condition) or the reference product (finasteride at 10 µM) for 24 hours. The *Lespedeza capitata* extract is an extract prepared according to Example 5 of the present invention and this extract is tested at two concentrations, 30 µg/ml and 100 µg/ml; it is a dry extract diluted in DMSO. Then the cells are treated for 24 hours by a medium containing $C^{14}$ testosterone and containing the compound to be tested or not. The culture supernatants are then collected for testosterone metabolism analyses.

The steroid molecules of the supernatant are extracted by a chloroform/methanol mixture. The organic phase is collected and DHT is separated by thin layer chromatography and by using a solvent system containing dichloromethane, ethyl acetate and methanol. Autoradiography is then carried out on the chromatography and the transformed testosterone is estimated by densitometric analyses. The raw data are analyzed by Microsoft Excel software. The statistical analysis is done by intergroup comparison with repeated measures ANOVA followed by a Dunnett's test.

In this study, the DHT/testosterone ratio is selected to represent the activity of the 5α-reductase enzyme. If this ratio decreases with the addition of a compound, this compound is then considered to be a 5α-reductase inhibitor. To be sure that this compound is truly specific for this enzyme, it is important to verify a reduction of the 5α-anrostane-3α, 17β-diol/testosterone ratio and the androstenedione/testosterone ratio and an increase of the 4-androstene-3,17-dione/testosterone ratio.

Results

Table 2 below shows the 5α-reductase activity (DHT/testosterone ratio) after an incubation of 24 h+24 h with the reference compound (finasteride) and the *Lespedeza capitata* extract.

|  | Conc | Mean | sem | % inh | sem | stats |
|---|---|---|---|---|---|---|
| Control | — | 0.31 | 0.10 | 0.0 | 7.2 | — |
| Finasteride | 10 µM | 0.02 | 0.01 | 94.2 | 1.4 | p < 0.01 |
| Lespedeza extract | 30 µg/ml | 0.23 | 0.05 | 21.8 | 8.6 | NS |
|  | 100 µg/ml | 0.11 | 0.01 | 59.6 | 9.0 | p < 0.05 |

Con: concentration; sem: standard error of the mean; % inh % of inhibition relative to the control condition; stats: statistic.

The treatment of human hair follicle dermal papilla cells with finasteride shows a very strong reduction in conversion of testosterone into DHT (reduction of the DHT/testosterone ratio). These results were expected and enable the test to be validated.

In the presence of *Lespedeza capitata* extract, the DHT/testosterone ratio is reduced in a concentration-dependent manner; this reduction (which reaches 60%) is statistically significant with a *Lespedeza capitata* concentration of 100 µg/ml Although the activity at 30 µg/ml was not qualified as statistically significant, it is still indicative.

The inventors thus clearly demonstrated that a *Lespedeza* extract has an inhibitor activity on 5α-reductase.

This *Lespedeza capitata* extract therefore exhibits an interesting activity for its use as an agent in the prevention and/or treatment of skin and hair disorders, in particular hair loss and/or scalp seborrhea and associated disorders.

Example 10: Inhibition of the Metabolic Activity and/or Proliferation of Dermal Papilla Cells by an Extract of Aerial Parts of *Lespedeza capitata*

The dermal papilla is located at the base of the hair follicle, deeply anchored in the cutaneous tissue. It has been known for a long time that dermal papilla cells play a key role in the growth of the hair follicle. Highly vascularized, the dermal papilla delivers nutrients to the hair and provides the molecular information necessary for the proliferation and differentiation of epithelial cells to produce a new hair at each cycle. Studies have shown that in healthy human hair follicles and in rat experiments, in a model of lesion-induced whisker regeneration, there is a correlation between the size of the dermal papilla (and also with the number of cells of the dermal papilla and the size of the hair shaft). This correlation is maintained in the context of a progressive hair loss, in which the size of the hair follicles and hair shafts is successively reduced with hair growth cycles. Moreover, the increase in the number of cells in the dermal papilla in a follicle can occur in part by the recruitment of new cells in the dermal papilla, but the proliferation of dermal papilla cells can also contribute to this expansion.

This study aims to evaluate the effect of an extract according to the present invention on the metabolic activity and/or proliferation of dermal papilla cells in order to measure the value of this extract in the field of hair loss prevention.

Experiments were conducted on dermal papilla cells of human hair follicles originating from three different donors.

The cells were inoculated onto 96-well plates and cultured for 24 hours in standard culture media. The medium is then replaced by a test medium (Follicle Dermal Papilla Cell Basal (HFDPC) Medium, Ref C-26500 from Promocell) containing the compound to be tested or not (control condition). A group with the same medium by supplemented by 5% of additional medium (Follicle Dermal Papilla Cell Growth Medium SupplementPack, Ref C-39620, Promocell) acts as a positive control. The *Lespedeza capitata* extract is an extract prepared according to Example 2 of the present invention and this extract is tested at two concentrations, 3 µg/ml and 10 µg/ml; it is a dry extract diluted in DMSO. Seventy-two hours later, the culture supernatants are collected and stored at −80° C.

Cell metabolic activity and proliferation are assessed by a colorimetric method, soluble tetrazolium salt (WIST-1), which is light red, turns red when reduced to formazan (test sold by Takara Clontech, under catalog number MK400). The raw data are analyzed by Microsoft Excel software. The statistical analysis is done by intergroup comparison with repeated-measures ANOVA followed by a Dunnett's test.

Results

Table 3 shows the results of the *Lespedeza* extract on metabolic activity and cellular proliferation.

|  | Concentration | Stim (%) | sem | stats |
|---|---|---|---|---|
| Control | — | 0 | 0.15 | — |
| Suppl medium | 5% | 60 | 28 | p < 0.05 |
| Lespedeza extract | 3 µg/ml | 51 | 4.3 | p < 0.05 |
|  | 10 µg/ml | 44 | 14.3 | p = NS |

Suppl medium: medium with supplement, permitting cell proliferation; sem: standard error of the mean; % stim: % of stimulation relative to the control condition; stats: statistic; OD: optical density.

Treatment of the dermal papilla cells by a supplemented medium induces significant activation of cell proliferation and/or metabolic activity. This result validates this model. The 3 µg/ml *Lespedeza capitata* extract induces a statistically-significant increase of cell proliferation and/or metabolic activity. This activation does not reach significance when the *Lespedeza capitata* is at 10 µg/ml, no doubt due to a great variability of results, but it is nevertheless at least indicative of the effect of the extract. The inventors thus clearly demonstrated that a *Lespedeza* extract has a stimulator activity on cell proliferation and/or metabolic activity. Therefore, this *Lespedeza capitata* extract has an interesting activity for its use in promoting hair growth, by strengthening and stimulating the hair lifecycle and by promoting hair regeneration.

Example 11: Assessment of the Aerial Parts of *Lespedeza capitata* on Human JAK1, JAK2 and JAK3 Inhibition JAK-STAT is a signalling pathway for transduction regulating growth, survival, differentiation and resistance to pathogens. This pathway mediates the effects of cytokines, interferons and growth factors. In mammals, the JAK family consists of four members: JAK1, JAK2, JAK3 and TYK2. In a study conducted in mouse hair follicles, it was shown that the JAK-STAT pathway is dynamically regulated in the hair cycle; the JAK-STAT pathway is activated during the catagen and telogen phases and repressed at the start of the anagen phase. Moreover, it was demonstrated in mice that a topical treatment in the telogen phase with JAK-STAT pathway inhibitors, including tofacitinib (JAK1/3>JAK2>TYK2) and ruxolitinib (JAK1/2>TYK2>JAK3), resulted in rapid return to the start of the anagen phase (Hare) et al., 2015 Sci. Adv.1, e1500973). In this same study it is also shown that inhibition of JAK-STAT in human hair follicles increases hair growth ex vivo. These data suggest that the JAK-STAT signalling pathway can be a new target to stimulate hair growth.

The goal of this example is to assess whether an extract according to the present invention can inhibit the JAK-STAT signalling pathway. This inhibition is assessed on human recombinant JAK1, JAK2 or JAK3 proteins.

Methods

The *Lespedeza capitata* extract is an extract prepared according to Example 5 of the present invention. This extract is diluted in DMSO and tested at various concentrations (0.1-1000 µg/ml). The positive controls (tofacitinib and ruxolitinib) are also assessed in this test.

The products to be tested are incubated with human recombinant JAK1, JAK2 or JAK 3 protein with a reaction buffer (Tris/HCl for JAK1, MOPS (3-morpholino-1-propane sulfonic acid) for JAK2 and JAK3), EDTA and specific peptide substrates. The phosphorylation reaction is then initiated by addition of a mixture of magnesium acetate and radiolabeled ATP (45 µM for JAK1 and JAK2 and 10 µM for JAK3). After incubation for 40 minutes at ambient temperature, the reaction is stopped by addition of phosphoric acid. Four washes with phosphoric acid and one with methanol are performed to elute small molecules including the labelled ATP. Finally, the radioactivity of the specific phosphorylated substrate is measured. The compounds are tested in three separate experiments, and duplicates are conducted for each experiment.

The $IC_{50}$ values, in µg/ml, for each recombinant JAK1, JAK2 and JAK3 protein according to the product tested are presented in Table 4 below:

| Compounds | JAK1 $IC_{50}$ (µg/ml) | JAK2 $IC_{50}$ (µg/ml) | JAK3 $IC_{50}$ (µg/ml) |
|---|---|---|---|
| Ruxolitinib | 0.00037 | 0.00023 | 0.0060 |
| Tofacitinib | 0.00087 | 0.00367 | 0.00057 |
| Lespedeza capitata extract | 24.8 | 146.5 | 3.9 |

The results obtained with the reference compounds (ruxolitinib and tofacitinib) conform to the expected ones. Indeed, these two compounds strongly inhibit JAK-STAT activity (between 97% and 100% maximum inhibition, with very low $IC_{50}$ values, of around a nanogram per milliliter). Ruxolitinib shows a greater affinity for JAK1 or JAK2 than for JAK3. Tofacitinib shows a greater affinity for JAK1 or JAK3 than for JAK2. These expected results validate this test.

The extract of the aerial part of *Lespedeza capitata* shows a strong inhibition of JAK1 (100% maximum inhibition) with an $IC_{50}$ value of 24.8 µg/ml, a strong inhibition of JAK2 (100% maximum inhibition) with a slightly higher $IC_{50}$ value of 146.5 µg/ml, and also a strong inhibition for JAK3 (100% maximum inhibition) with an $IC_{50}$ value of 3.9 µg/ml.

This test demonstrates that a *Lespedeza capitata* extract induces inhibition of tyrosine kinase activity (with a greater affinity for JAK3), revealing a pharmacological activity of interest to promote hair growth.

Example 12: Confirmation of the JAK-STAT Pathway Inhibitor Activity of an Extract of the Aerial Part of *Lespedeza capitata* at the Cellular Level The goal of this example is to confirm the inhibitor activity of an extract of *Lespedeza capitata* on the JAK-STAT signalling pathway in a cell model, follicular keratinocytes of the outer epithelial sheath of the hair follicle (outer root sheath (ORS) model). In this model, interleukin IL-6 is used to activate the JAK1/2-STAT3 pathway by activation of IL-6 and GP130 receptors which are both expressed in this hair follicle epithelial sheath. Il-6 is a cytokine that acts as a hair growth cycle inhibitor. Its overexpression in a transgenic mouse model leads to delayed hair growth. Moreover, in androgenetic alopecia, IL-6 would be overexpressed in dermal papilla cells under the influence of androgens (Kwack et al., 2012, J Invest Dermatology 132(1): 43-9). It has also been reported that IL-6 delays hair follicle growth in humans.

Method

The study is performed on follicular keratinocytes of the outer epithelial sheath of the hair follicle (outer root sheath (ORS) model). The keratinocytes are cultured in 96-well plates in an appropriate medium (CnT-PR from CelINTech). Twenty-four hours later, the cells are washed with an alkaline phosphate buffer (PBS) and the medium is exchanged for CnT-PR-H (standard maintenance medium for primary human keratinocytes). After 48 hours, the cells are treated for 1 hour with the compound to be tested (*Lespedeza capitata* extract at 30 and 100 µg/ml diluted in DMSO) and the reference compounds (ruxolitinib and tofacitinib at 5 µM, both diluted in DMSO). The *Lespedeza capitata* tested is an extract prepared according to Example 5 of the present invention. Then the stimulation treatment by IL-6 is conducted at 100 ng/ml for 15 minutes.

All the conditions are tested on cells from n=3 different donors. The *Lespedeza capitata* extracts are tested in n=3 different experiments, the control conditions, stimulation and with reference compounds are conducted in n=6 experiments. For each experiment, the data are produced in triplicate.

JAK activity is estimated by assessing the degree of phosphorylation of STAT3 protein. Statistical analysis is done by a parametric test after verification of the normality and equivalence of variance, otherwise a nonparametric test is chosen.

Results

The results are summarized in Table 5 below.

| Condition | Groups | % of STAT phosphorylated | | |
|---|---|---|---|---|
| | | Mean | sem | % inh |
| — | Control | 100 | 0.0 | 100 |
| IL-6 | Control | 116 | 1.0 | 0 |
| IL-6 | Ruxolitinib | 102 | 3.5 | 85 |
| IL-6 | Tofacitinib | 99 | 2.4 | 104 |
| IL-6 | Lespedeza capitata (30 µg/ml) | 71 | 7.2 | 285 |
| IL-6 | Lespedeza capitata (100 µg/ml) | 59 | 3.7 | 366 | sem: standard error of the mean; % inh: percentage of inhibition.

The treatment of keratinocytes with IL-6 induces a significant increase in the degree of STAT3 phosphorylation. This increase reaches 16% and is statistically significant ($p<0.05$). The reference compounds (ruxolitinib and tofacitinib tested at 5 µM) significantly reduce the degree of STAT3 phosphorylation, respectively by 85% and 104%, p<0.05 for ruxolitinib and p<0.01 for tofacitinib. These expected results validate this test.

The *Lespedeza capitata* extract at both concentrations tested significantly (p<0.01 for both concentrations) and very markedly inhibited the degree of STAT3 phosphorylation inducted by stimulation with IL-6.

The inventors thus demonstrate the value of an extract of the aerial part of *Lespedeza capitata* in promoting hair regrowth.

The invention claimed is:

1. Method for treating at least one skin and hair disorder chosen from among alopecia, a scalp seborrhea and combinations thereof, comprising the application to a person in need thereof of a *Lespedeza capitata* extract, wherein the extract is obtained from the aerial parts of *Lespedeza capitata* plant following extraction with an extraction solvent comprising a hydroalcoholic mixture, wherein the hydroalcoholic mixture is a mixture of water with a C1 to C5 alcohol.

2. Method according to claim 1, wherein the aerial parts are selected from the group consisting of stems, branches, leaves, fruits, seeds and flowers.

3. Method according to claim 1, wherein the extraction solvent is an ethanol/water mixture.

4. Method according to claim 1, wherein the extract comprises from 2 to 40% by weight of total polyphenols on a dry weight basis of the extract.

5. Method according to claim 1, wherein alopecia is chosen in the group consisting of androgenetic alopecia, reactive alopecia, postmenopausal alopecia and alopecia aerata.

6. Method according to claim 1, wherein the application is done with a dermatological composition comprising the *Lespedeza capitata* extract and at least one cosmetically or dermatologically-acceptable excipient.

* * * * *